(12) United States Patent
Noblitt et al.

(10) Patent No.: US 6,962,574 B1
(45) Date of Patent: Nov. 8, 2005

(54) THERAPEUTIC AGENT DELIVERY DEVICE

(75) Inventors: Niles L. Noblitt, Mountain Lakes, NJ (US); Richard Craig Blaschke, Leesburg, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 123 days.

(21) Appl. No.: 10/461,806

(22) Filed: Jun. 13, 2003

(51) Int. Cl.$^7$ .......................... A61M 31/00; A61F 2/00
(52) U.S. Cl. ........................... 604/60; 424/426
(58) Field of Search .................. 604/51, 59, 60–64, 604/890.1; 424/422, 426, 428, 438; 623/1.11, 623/1.42, 1.44, 1.45; 433/173

(56) References Cited

U.S. PATENT DOCUMENTS

| | | | | |
|---|---|---|---|---|
| 2,721,387 A | * | 10/1955 | Ashuckian | .................... 433/173 |
| 4,142,526 A | * | 3/1979 | Zaffaroni et al. | ............ 424/424 |
| 4,687,480 A | * | 8/1987 | Laby et al. | .................. 424/438 |
| 4,773,858 A | * | 9/1988 | Marquez | ..................... 433/173 |
| 5,342,348 A | | 8/1994 | Kaplan | |
| 5,443,458 A | | 8/1995 | Eury | |
| 5,512,291 A | | 4/1996 | Li | |
| 5,766,710 A | | 6/1998 | Turnlund et al. | |
| 5,769,883 A | | 6/1998 | Buscemi et al. | |
| 5,968,047 A | | 10/1999 | Reed | |
| 6,013,853 A | | 1/2000 | Athanasiou et al. | |
| 6,228,111 B1 | | 5/2001 | Törmälä et al. | |
| 6,248,112 B1 | | 6/2001 | Gambale et al. | |
| 6,263,880 B1 | * | 7/2001 | Parker et al. | ............... 128/898 |
| 6,363,938 B2 | | 4/2002 | Saadat et al. | |
| 6,652,582 B1 | * | 11/2003 | Stinson | ..................... 623/1.39 |
| 2001/0014813 A1 | | 8/2001 | Saadat et al. | |
| 2001/0037117 A1 | | 11/2001 | Gambale et al. | |

* cited by examiner

Primary Examiner—Sharon Kennedy
(74) Attorney, Agent, or Firm—Harness, Dickey & Pierce, P.L.C.

(57) ABSTRACT

A biological therapeutic delivery device is provided. In one preferred embodiment, the invention includes a device for effectuating localized tissue injury comprised of a resorbable body having at least one therapeutic agent and a retention device to anchor the agent within a tissue, the therapeutic agent being released into the tissue as the body resorbs. In an additional preferred embodiment, the invention includes a device for effectuating localized tissue injury comprised of a resorbable body having a cavity containing a therapeutic agent and a series of projections extending from the body to anchor the body in a tissue, the therapeutic agent being released into the tissue as the body resorbs.

27 Claims, 2 Drawing Sheets

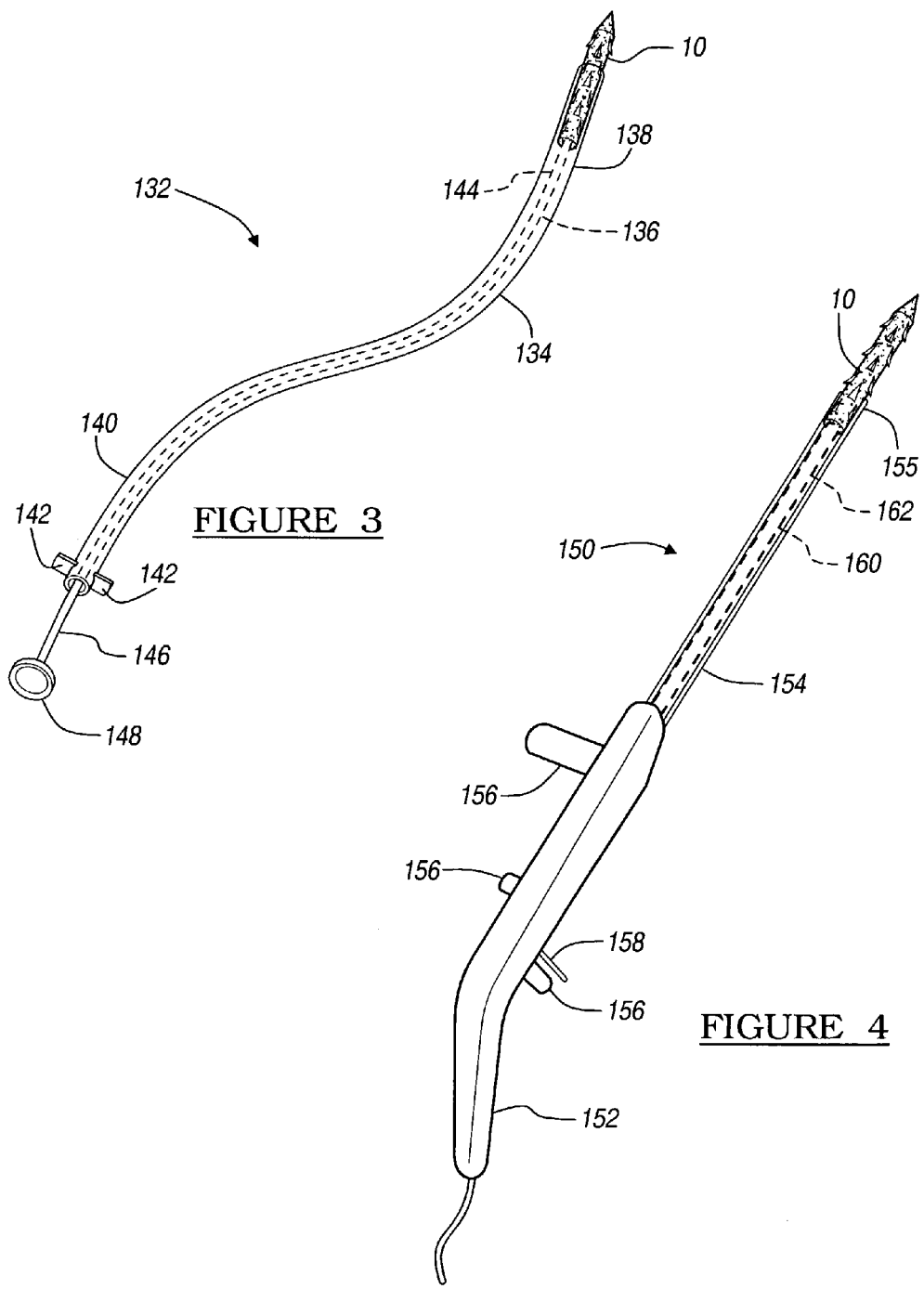

THERAPEUTIC AGENT DELIVERY DEVICE

FIELD OF THE INVENTION

The present invention generally relates to devices for delivering biological therapeutic agents. In particular, the present invention relates to a biological therapeutic agent delivery vehicle that induces a local tissue injury at an implantation site.

BACKGROUND OF THE INVENTION

Ischemic heart disease is a leading cause of death in the United States. Ischemic heart disease is a term given to heart-related conditions caused by decreased blood flow to the heart. This disease is most commonly caused by blockages in the coronary arteries, the blood vessels that provide blood to the heart. The coronary arteries most often become narrowed or blocked by a gradual build-up of atherosclerotic plaque. If the plaque significantly narrows the lumen or channel of the artery, blood flow is significantly reduced and the heart muscle does not receive the amount of blood flow necessary to meet its needs. Severe symptoms of cardiac ischemia include chest pain, heart attack, or arrhythmias.

One approach used to treat ischemic heart disease is therapeutic angiogenesis, the ability to pharmacologically induce new blood vessel growth. In therapeutic angiogenesis, new blood supplies are established for the heart to increase tissue survival and function, as well as relieve patient symptoms, such as angina. Angiogenic activity is supplied by introducing one or more of a variety of different angiogenic stimulating therapeutic agents, such as growth factors, to the heart.

The angiogenic stimulating therapeutic agents may be administered either alone or as a combination therapy with surgery or transmyocardial revascularization (TMR). In TMR, one or more small wounds are created in an ischemic heart in order to stimulate angiogenesis as part of the healing process. Delivery of angiogenic stimulating therapeutic agents to the wound sites allows for enhanced angiogenesis. Conventionally, a laser is used to create the small wounds in the heart tissue. Once the wounds are created, the therapeutic agents are introduced using a syringe.

While current therapeutic angiogenesis and TMR techniques are adequate, they are subject to improvement. Specifically, there is a need for an improved device and method for creating small wounds in the heart. Further, there is a need for an improved device and method for delivering therapeutic agents to the wounds.

SUMMARY OF THE INVENTION

In accordance with the present invention, a device for delivering biological therapeutic agents is provided. In one embodiment, the invention includes a device for effectuating localized tissue injury comprising a body having at least one therapeutic agent and at least one retention device to anchor the device in a tissue, the therapeutic agent being released into the tissue while the device is seated within the tissue. In another embodiment, the invention includes a system for effectuating localized tissue injury comprising a therapeutic device having a therapeutic agent, and an implantation tool for implanting the device within a tissue, wherein the therapeutic agent is released into the tissue. In still another embodiment, the invention includes a method for effectuating angiogenesis comprising creating a localized injury within a tissue, inserting a therapeutic device containing at least one therapeutic agent within the localized injury, and introducing the therapeutic agent to the injury to promote angiogenesis.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 3 is a perspective view of an insertion tool equipped with the device of FIG. 1;

FIG. 4 is a perspective view of another insertion tool equipped with the device of FIG. 1.

DETAILED DESCRIPTION

The following description of the embodiments is merely exemplary in nature and is in no way intended to limit the invention, its application, or uses. Moreover, while the present invention is discussed in relation to the delivery of a therapeutic agent to a heart, it may also be directed to any other part of the body.

Figure 1:
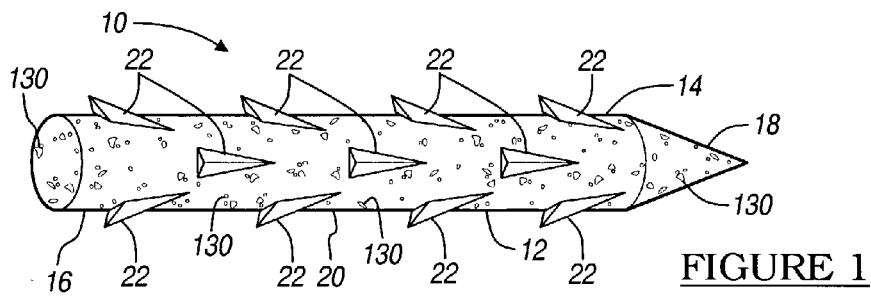
FIG. 1 is a side view of a device according to an embodiment of the present invention for delivering biological therapeutic agents to a tissue of interest.

A device according to an embodiment of the present invention for both penetrating a tissue and delivering a biological therapeutic agent to the tissue is illustrated in FIG. 1 at 10. The device 10 includes a main body 12 having a first end 14 and a second end 16. The main body 12 is shaped as an elongated solid cylinder, or any other appropriate shape. The first end 14 includes a pointed tip 18. The first end 14 may include a blunt tip if desired.

Extending from an exterior surface 20 of the main body 12 is at least one retention device that maintains the device 10 in its intended position. While the retention device is illustrated as a projection 22, the projection 22 is used for exemplary purposes only as the retention device may take the form of a variety of different devices. The projections 22 may be of any suitable shape or size but are generally canted from the first end 14 to the second end 16 of the main body 12. The projections 22 are canted such that each projection 22 is most narrow, and nearly flush with the exterior surface 20, at the end of the projection closest to the first end 14 and each projection 22 is widest, and raised from the exterior surface 20, at the end of the projection closest to the second end 16. The shape of the projections 22 facilitates insertion of the device 10 at its desired location within the tissue and helps retain the device 10 within the tissue by engaging the tissue. The shape, number, and location of the projections 22 may vary according to the intended application of the device 10.

Figure 2:
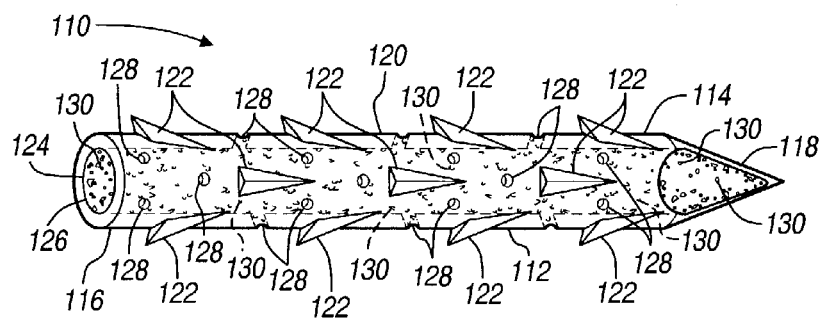
FIG. 2 is a side view of a device according to another embodiment of the present invention for delivering biological therapeutic agents to a tissue of interest.

Another therapeutic insertion device according to another embodiment of the present invention is illustrated in FIG. 2 at 110. Like the device 10, the device 110 includes a cylindrical main body 112 having a first end 114, a second end 116, a pointed tip 118 at the first end 114, and an exterior surface 120 with at least one retention device for securing the device 110 within a tissue of interest. The retention device is illustrated as projections 122. However, the projections 122 are illustrated for exemplary purposes only as the retention device may take the form of a variety of different devices. The projections 122 are substantially similar to the retention projections 22 of the device 10 and thus the description of the projections 22 provided above also accurately describes the retention projections 122.

The device 110 further includes a center bore 124 that extends through at least a portion of the main body 112. Optionally, the center bore 124 extends entirely through the main body 112 and into the tip 118. The center bore 124 has an opening 126 at the second end 116 of the device 110.

The exterior surface 120 of the device 110 optionally includes one or more ports 128. The ports 128 extend from the exterior surface 120 to the center bore 124 and provide communication between the center bore 124 and the exterior surface 120. While FIG. 2 illustrates the ports 128 as being located on the exterior surface 120 of the main body 112, the ports 128 may also be present within the tip 118. The number and size of the ports 128 may vary depending on the particular application for which the device 110 is used.

The devices 10 and 110 may be formed of a suitable resorbable material using conventional molding processes. The particular resorbable material used and its composition depends on the intended application of the devices 10 and 110. The resorbable material used is generally compatible with the target tissue, resorbs within the target tissue at a desired rate, and is sufficiently rigid to penetrate the target tissue if it is desired that penetration be effectuated by either device 10 or device 110, rather than another instrument. An example of a resorbable material that may be used is LACTOSORB® from Biomet, Inc. of Warsaw, Ind. LACTOSORB® is substantially amorphous (i.e., without crystallinity) and its degradation is uniform. LACTOSORB® is a co-polymer synthesized from all-natural ingredients and is conventionally comprised of 82% L-lactic acid and 18% glycolic acid. However, it must be realized that the particular composition used may vary according to the target tissue, the particular application of the device 10, and the rate of resorbtion desired.

The device 10 and the device 110 each further include one or more therapeutic agents 130. The specific therapeutic agents 130 used depends upon the particular application of the devices 10 and 110. For example, if the devices 10 or 110 are used in therapeutic angiogenesis, the therapeutic agent may be a fibroblast growth factor, a vascular endothelial cell growth factor, or any other appropriate agent.

As illustrated in FIG. 1, the device 10 includes one or more of the therapeutic agents 130 incorporated within at least a portion of the structure and generally within the main body 12 and the tip 18. Specifically, either during or before the molding of the device 10, the therapeutic agent 130 is intermixed with the resorbable material. Thus, when the device 10 is molded from the resorbable material containing the therapeutic agent 130, the therapeutic agent 130 is incorporated within the structure of the device 10.

As illustrated in FIG. 2, the device 110 includes one or more therapeutic agents 130 within the bore 124. The therapeutic agents 130 are inserted within the center bore 124 through the opening 126 using any suitable device, such as a syringe. If the device 110 includes one or more of the ports 128, the therapeutic agents 130 may exit the device 1 10 through the ports 128.

Figure 5:
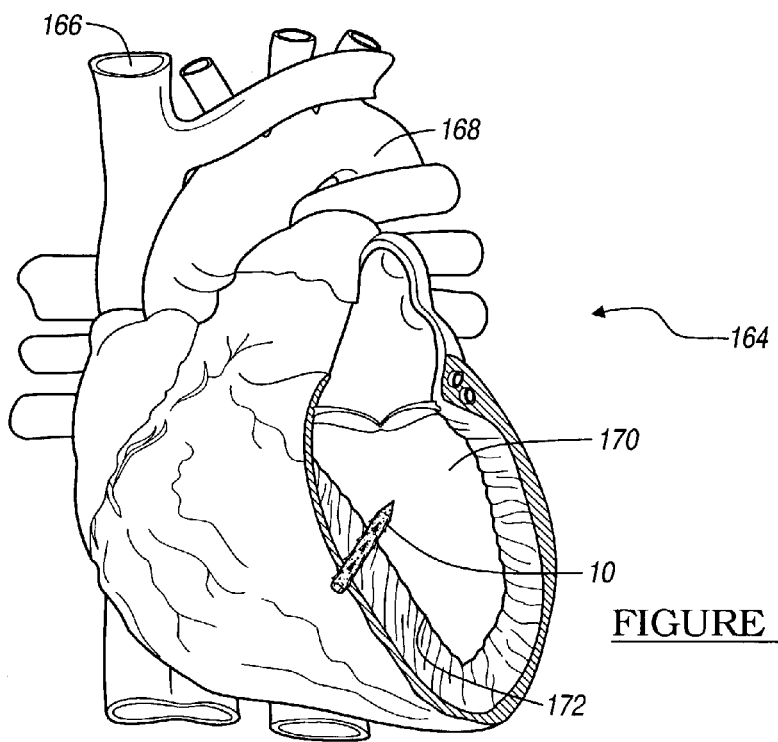
FIG. 5 is a partially cross-sectioned side view of a human heart with the device of FIG. 1 inserted within the heart.

With reference to FIGS. 3 through 5, the implantation of the device 10 is described. As the implantation of the device 10 is substantially similar to the implantation of the device 110, the below description of the implantation of the device 10 also adequately describes the implantation of the device 110.

A delivery plunger 132 for delivering the device 10 to an implantation site is illustrated in FIG. 3. The delivery plunger 132 generally includes a delivery tube 134 and a pushrod 136. The delivery tube 134 is a flexible elongated tube having a first end 138 and a second end 140. Both the first end 138 and the second end 140 are open. The first end 138 may be a pointed or sharp open tip (not shown). The second end 140 includes a pair of handles 142. The pushrod 136 includes a first end 144 and a second end 146. The second end 146 includes a knob 148.

The pushrod 136 is seated within the delivery tube 134. The pushrod 136 is actuated in and out of the delivery tube 134 by an operator preferably grasping both of the handles 142 of the delivery tube 134 and the knob 148 of the pushrod 136. Mounted at the first end 144 of the pushrod 136 is the device 10. As the pushrod 136 is pushed through the delivery tube 134 the device 10 is also pushed through the tube 134 causing the device 10 to exit the second end 140 of the delivery tube 134, as illustrated in FIG. 3. The flexible structure of the delivery tube 134 makes the delivery plunger 132 well suited for use in arthroscopic procedures.

A delivery gun for installing the device 10 is illustrated in FIG. 4 at 150. The gun 150 generally includes a handle 152 and a rigid shaft 154 extending from the handle 152. The rigid shaft 154 is hollow and terminates at a distal end 155. The distal end 155 is open and may be pointed. The handle 152 includes a series of tabs 156 to assist manipulation of the gun 150 and a trigger 158 for operating the gun 150. Extending through the shaft is a rod 160. The rod 160 has a terminus 162 to which the device 10 is mounted. The rod 160 is actuated within the shaft 154 in response to movement of the trigger 158 by an operator. Movement of the trigger 158 pushes the rod 160 through the shaft 154 causing the device 10 mounted to the terminus 162 to exit the shaft 154, as illustrated in FIG. 4, to permit delivery of the device 10 to a desired location.

The device 10 may also be implanted by an extension rod (not shown) that directly contacts the device 10 at one end of the rod and is manipulated by a surgeon at an opposite end. The extension rod does not require the use of a guide tube. The extension rod provides a simplified and easy to use implantation device comprised of a minimal number of parts.

Using the delivery plunger 132, the delivery gun 150, the extension rod, or any other suitable implantation instrument, the device 10 is directed to and inserted within a desired tissue, such as tissues of a human heart, illustrated in FIG. 5 at 164. It must be noted that the heart 164 is used for explanatory purposes only and is but one of many different tissues that may be impregnated by the device 10 for delivery of the therapeutic agent 130.

As illustrated in FIG. 5, the heart 164 is generally comprised of a superior vena cava 166, an aorta 168, a left ventricle 170, and a right ventricle (not shown). The device 10 may be inserted within the heart 164 at any suitable location depending upon the procedure being performed and the composition of the device 10. In FIG. 5 the device 10 is illustrated as being inserted within a wall 172 of the left ventricle 170.

To insert the device 10 within the wall 172 of the left ventricle 170, the device 10 is first directed over the portion of the wall 172 where insertion of the device 10 is desired using, for example, the delivery plunger 132, the delivery gun 150, or the extension rod. Once the device 10 is in the proper position over the wall 172, the device 10 is inserted within the wall 172 by, for example, depressing the knob 148 or activating the trigger 158 to cause the device 10 to be ejected from either the delivery tube 134, of the delivery plunger 132, or the shaft 154, of the delivery gun 150, respectively. Further, the device 10 may be inserted within the wall 172 using the extension rod, thus eliminating the need for any type of delivery tube or shaft.

Upon insertion of the device 10 within the wall 172, the device 10 creates a localized injury within the wall 172 and the projections 22 engage the wall 172 to prevent the device from becoming dislodged or migrating from within the wall 172. Alternatively, the localized injury may be created by the implantation device, rather than the device 10, if the delivery tube 134 or the shaft 134 are sharpened or pointed. The creation of one or more localized injuries in the heart 164 stimulates angiogenesis as part of the healing process of the injuries and is known as transmyocardial revascularization (TMR). After the device 10 is inserted within the wall 172, the device 10 resorbs within the heart 164 due to its composition. As the device 10 resorbs, the therapeutic agents 130 within the device 10 are released and received by the area in the wall 172 surrounding the device. The therapeutic agents 130 enhance both the healing process and angiogenesis.

Operation of the device 110 is substantially similar to the operation of device 10. Using either the delivery plunger 132 or the delivery gun 150, the device 110 is inserted within the wall 172 of the heart 164. Once the device 110 is within the wall 172, the therapeutic agents 130 within the bore 124 begin to seep out from within the bore 124 through the ports 128. While a portion of the therapeutic agents 130 seep through the ports 128 with the surface 120 of the device 110 still intact, the remainder of the therapeutic agents 130 are released from the device 10 when the surface 120 degrades during resorbtion as the center bore 124 is no longer intact and able to contain the therapeutic agents 130.

In addition to the preferred embodiments discussed above, it may be appreciated that the invention may include additional aspects and features. For example, while the device 10 is described above as having a solid main body 12 and tip 18, the device 10 may also include a center bore to hold the therapeutic agents 130 that extends through the main body 12 and into the tip 18, similar to the bore 124 of the device 110. Further, the device 10 may include pores 128 to permit the release of the therapeutic agents 130 from the bore. Still further, the device 110 may be molded from a resorbable material containing the therapeutic agents 130, thus incorporating the therapeutic agents 130 within the structure of the device 110 as is known in the art. In addition to the delivery plunge 132 and the delivery gun 150, the device 10 and the device 110 may be implanted using a multi-fire, gas operated, delivery gun (not shown), which can insert in excess of 50 of the devices 10 and 110 in a particular area. Finally, the devices 10, 110 may be non-resorbable. If the devices 10, 110 are non-resorbable they may be inserted within the desired tissue for a suitable period of time to permit the release of the therapeutic agents 130 and then removed from the tissue once the therapeutic agents 130 have been released, if removal is desired.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A device for effectuating localized tissue injury comprising:
    a body having at least one therapeutic agent, said body having a first end and a second end opposite said first end; and
    a plurality of retention devices protruding from said body between said first end and said second end for maintaining said device in a desired position within a tissue;
    said retention devices each having a forward portion proximate said first end and a rear portion distal to said first end;
    said forward portion being more narrow than said rear portion;
    said rear portion protruding further from said body than said forward portion;
    wherein said therapeutic agent is released into said tissue while said device is seated within said tissue.

2. The device of claim 1, wherein said rear portion extends from said body to a pointed tip.

3. The device of claim 1, wherein said retention device is canted from said first end of said device to said second end of said device opposite said first end to facilitate insertion of said device within said tissue.

4. The device of claim 1, wherein said device is resorbable.

5. The device of claim 1, wherein said first end is pointed to facilitate insertion of said device within said tissue.

6. The device of claim 1, wherein said body defines a center cavity.

7. The device of claim 6, wherein said center cavity contains said therapeutic agent.

8. The device of claim 6, wherein said body is comprised of at least one port defining a passageway from said cavity to an exterior of said body.

9. The device of claim 1, wherein said therapeutic agent is molded within said body.

10. The device of claim 1, wherein said therapeutic agent is a fibroblast growth factor.

11. The device of claim 1, wherein said therapeutic agent is a vascular endothelial cell growth factor.

12. The device of claim 1, wherein said tissue is a heart tissue.

13. A system for effectuating myocardial tissue injury including a device comprising:
    a resorbable body having a first end and a second end opposite said first end;
    at least one of said first end and said second end is pointed to facilitate insertion of said device within the myocardial tissue;
    a cavity defined by said body;
    a plurality of ports extending through said body and providing communication between said cavity and an exterior of said device;
    a therapeutic agent present in said cavity;
    a plurality of retention devices on an exterior of said body between said first end and said second end for retaining said therapeutic device in a desired position within said tissue and to promote tissue injury;
    said retention devices each having a first portion and a second portion, said first portion proximate to said first end and said second portion distal to said first end;
    said first portion is more narrow than said second portion;
    said second portion protrudes further from said body than said first portion;

said retention devices are arranged in linear columns extending between said first end and said second end and spaced apart at regular intervals;

wherein said therapeutic agent is released from said cavity, via said ports, into the myocardial tissue when said device is seated in the myocardial tissue.

14. The system of claim 13, wherein said projection is canted from said first end to said second end to facilitate insertion and retention of said device within said tissue.

15. The system of claim 13, wherein said therapeutic agent is molded within said device.

16. The system of claim 13, wherein said therapeutic agent is a fibroblast growth factor.

17. The system of claim 13, wherein said therapeutic agent is a vascular endothelial cell growth factor.

18. The system of claim 13, further comprising a tool for implanting said device in the myocardial tissue that creates a localized tissue injury within said tissue.

19. The system of claim 13, wherein said therapeutic device creates a localized tissue injury within said tissue.

20. The system of claim 13, wherein said therapeutic agent is released into said tissue as said therapeutic device resorbs within said tissue.

21. The device of claim 13, wherein said second end of said retention device extends from said body to a pointed tip.

22. The device of claim 13, wherein said retention devices of neighboring columns are at different distances from said first end.

23. A method for effectuating angiogenesis comprising:
creating a localized injury within a tissue;
inserting a therapeutic device within said localized injury to promote angiogenesis, said therapeutic device including:
a body;
a first end of said body;
a second end of said body opposite said first end;
a plurality of retention devices extending from said body between said first end and said second end;
said retention devices having a first portion proximate to said first end and a second portion distal to said first end, said first portion being more narrow than said second portion, said second portion extending from said body to a greater distance than said first portion, said retention devices arranged in linear columns extending between said first end and said second end, said retention devices spaces apart at regular intervals;
a cavity defined by said body;
a plurality of ports extending through said body to provide communication between said cavity and an exterior of said body;
a therapeutic agent present in said cavity, said therapeutic agent is released from said cavity into the myocardial tissue via said ports when said device is seated in the myocardial tissue.

24. The method of claim 23, wherein said therapeutic agent is introduced to said injury as said therapeutic device resorbs within said tissue.

25. The device of claim 23, wherein said retention device is canted from said first end of said device to said second end of said device opposite said first end to facilitate insertion of said device within said tissue.

26. The method of claim 23, wherein said second portion of said retention devices extend from said body to a pointed tip.

27. The method of claim 23 wherein said retention devices of neighboring columns are at different distances from said first end.

* * * * *